United States Patent
Baumgart

(10) Patent No.: US 8,150,127 B2
(45) Date of Patent: Apr. 3, 2012

(54) METHOD FOR AUTOMATICALLY SYNCHRONIZING THE REVIEW OF TWO DSA SCENES

(75) Inventor: John Baumgart, Hoffman Estates, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 563 days.

(21) Appl. No.: 12/370,252

(22) Filed: Feb. 12, 2009

(65) Prior Publication Data

US 2009/0297004 A1  Dec. 3, 2009

Related U.S. Application Data

(60) Provisional application No. 61/056,534, filed on May 28, 2008.

(51) Int. Cl.
*G06K 9/00* (2006.01)
(52) U.S. Cl. ........................................ 382/130
(58) Field of Classification Search .................. 382/128, 382/130–132; 600/1–15
See application file for complete search history.

(56) References Cited

U.S. PATENT DOCUMENTS

| | | | | |
|---|---|---|---|---|
| 7,545,967 | B1 * | 6/2009 | Prince et al. ................. | 382/130 |
| 2006/0093198 | A1 * | 5/2006 | Fram et al. .................... | 382/128 |
| 2006/0257006 | A1 * | 11/2006 | Bredno et al. ................ | 382/128 |

OTHER PUBLICATIONS

Alexandru Condurache, Chapter "Fast Detection and Processing of Arbitrary Contrast Agent Injections in Coronary Angiography and Fluoroscopy" in Book: Bildverarbeitung für die Medizin 2004: Algorithmen, Systeme, Anwendungen, 2004, Springer, pp. 5-9.*
Co-pending U.S. Appl. No. 12/199,894, filed Aug. 28, 2008, George Kramp, et al.
Co-pending U.S. Appl. No. 12/260,501, filed Oct. 29, 2008, John Baumgart, et al.

* cited by examiner

*Primary Examiner* — Georgia Y Epps
*Assistant Examiner* — Renee Naphas
(74) *Attorney, Agent, or Firm* — Alexander J Burke

(57) ABSTRACT

A system automatically synchronizes display of adjacent different medical image sequences of an anatomical portion derived for use in Angiography or another medical procedure. The system includes an imaging system for acquiring first and second sets of data at different stages of a treatment procedure representing corresponding first and second image sequences individually comprising multiple temporally sequential individual images of vessels of a portion of patient anatomy. The sequential individual images encompass introduction of a contrast agent into patient vessels. A display presents the first and second image sequences in substantially adjacent display areas to facilitate user comparison. A contrast agent detector automatically analyzes the first and second image sequences to identify a first image frame in both the first image sequence and the second image sequence indicating presence of a contrast agent. A display processor automatically synchronizes presentation of the first image sequence and the second image sequence in respective areas of the substantially adjacent display areas in response to identification of the first image frame and relative to introduction of contrast agent and enables a user to synchronously increment through image frames of both the first image sequence and the second image sequence, one frame at a time.

19 Claims, 4 Drawing Sheets

METHOD FOR AUTOMATICALLY SYNCHRONIZING THE REVIEW OF TWO DSA SCENES

This is a non-provisional application of provisional application Ser. No. 61/056,534 filed May 28, 2008, by J. Baumgart.

FIELD OF THE INVENTION

This invention concerns a system for automatically synchronizing display of adjacent different medical image sequences of an anatomical portion derived for use in Angiography, for example, or another medical procedure.

BACKGROUND OF THE INVENTION

Digital Subtraction Angiography (DSA) is used in X-ray imaging to enhance visualization of a vessel structure in patient anatomy. In DSA, a mask image representing background information of a portion of anatomy in the absence of a contrast agent, is subtracted from an image of the same portion of anatomy with the vessel structure perfused by a contrast agent. The subtraction removes background detail and enhances the visualization of the vessel structure to improve catheterization and other procedures. It is useful, for example, to compare two DSA image sequence acquisitions in which one image sequence of a vessel structure is acquired before treatment and a second image sequence of the vessel structure is acquired after treatment to evaluate the effectiveness of treatment during interventional angiography such as a balloon catheterization. In order to perform this comparison, a point at which the two DSA image sequences are synchronized is selected. This is typically the time at which a contrast agent is first injected into a patient for each image sequence. However, the time of first contrast injection may vary between different image sequences so selection of the synchronization point is usually performed manually before the effectiveness of treatment may be evaluated based on side-by-side comparison of pre- and post-treatment image sequence acquisitions. Such manual selection is a slow, burdensome and error prone process. A system according to invention principles addresses these deficiencies and associated problems.

SUMMARY OF THE INVENTION

A system automatically determines a synchronization point in two different medical image sequences, e.g., DSA image sequences that typically represent pre- and post-treatment image sequence acquisitions. A system automatically synchronizes display of adjacent different medical image sequences of an anatomical portion derived for use in Angiography or another medical procedure. The system includes an imaging system for acquiring first and second sets of data at different stages of a treatment procedure representing corresponding first and second image sequences individually comprising multiple temporally sequential individual images of vessels of a portion of patient anatomy. The sequential individual images encompass introduction of a contrast agent into patient vessels. A display presents the first and second image sequences in adjacent areas to facilitate user comparison. A contrast agent detector automatically analyzes the first and second image sequences to identify a first image frame in both the first image sequence and the second image sequence indicating presence of a contrast agent. A display processor automatically synchronizes presentation of the first image sequence and the second image sequence in respective areas of the substantially adjacent display areas in response to identification of to the first image frame and relative to introduction of contrast agent and enables a user to synchronously increment through image frames of both the first image sequence and the second image sequence, one image at a time.

DETAILED DESCRIPTION OF THE INVENTION

Figure 1:
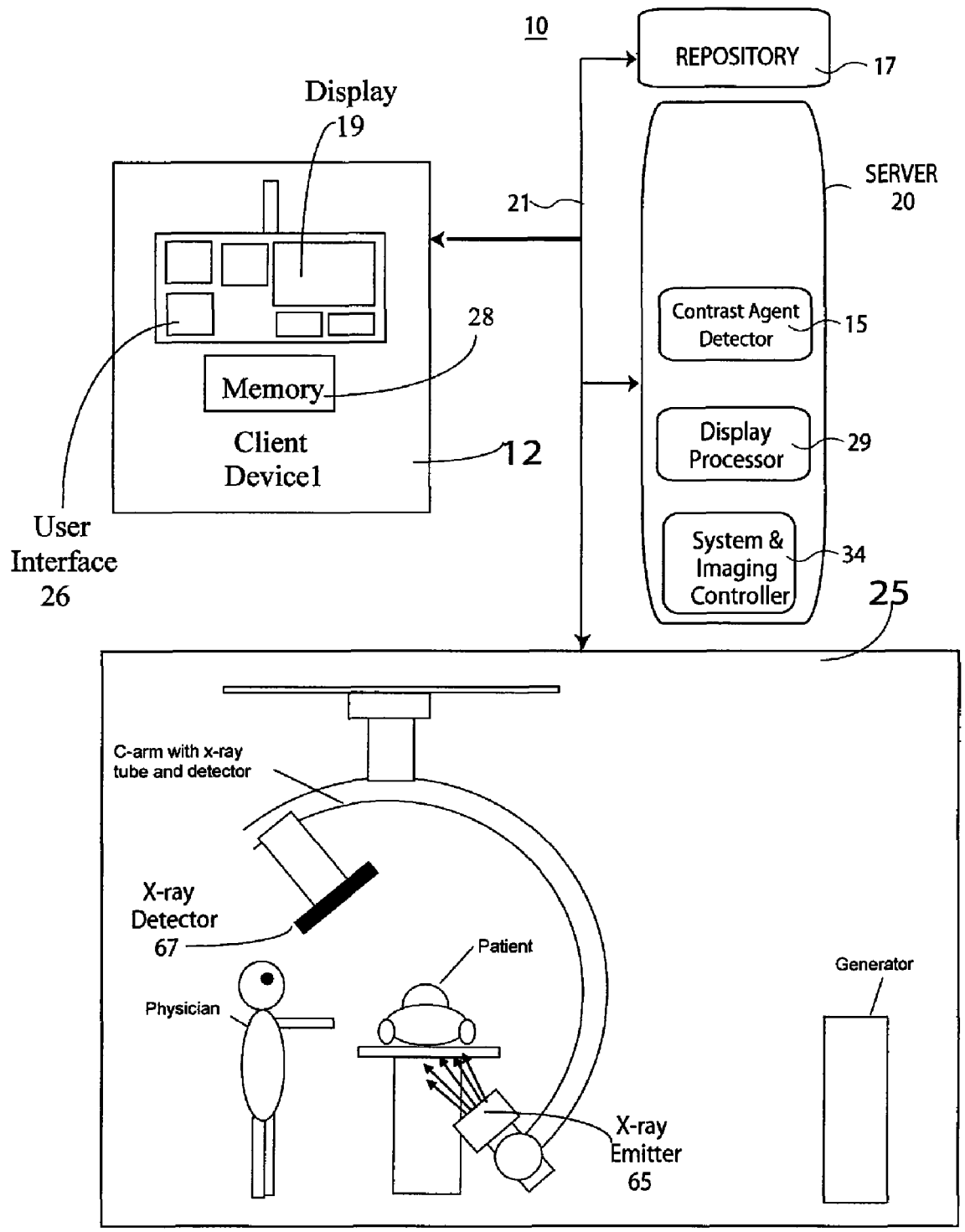
FIG. 1 shows a system for automatically synchronizing display of adjacent different medical image sequences of a portion of patient anatomy, according to invention principles.

A system automatically determines a synchronization point in two different medical image sequences, e.g., DSA image sequences that typically represent image sequence acquired pre- and post-treatment. The system analyzes data representing different individual DSA image sequences to determine a first image frame in each sequence that contains contrast agent. The identification of a first image frame containing contrast agent may be performed as indicated in co-pending application Ser. No. 12/199,894 entitled "An Image Data Subtraction System Suitable for Use in Angiography" or by another known method. In response to analysis of two DSA image sequences by the system, the image frames automatically chosen as the first contrast image frames in both sequences are used as a synchronization point for the two image sequences. In other embodiments, an image relative to the chosen images may be selected as the synchronization point or the system may also accommodate a heart cycle or other synchronization signal. Further a user interface enables a user to alter a synchronization point if desired. In one embodiment system 10 synchronizes different image sequences based on an image frame derived from the time of contrast injection, such as an image frame preceding a frame containing contrast agent. For reviewing DSA image sequences, this may present a user with a solid grey display of a vessel structure in different image sequences at a synchronization point that provides a visual comparison cue.

A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be electrically coupled with any other processor enabling interaction and/or communication there-between. A processor comprising executable instructions may be electrically coupled by being within stored executable instruction enabling interaction and/or communication with executable instructions comprising another processor. A user interface processor or generator is a known element comprising electronic circuitry or software or a combination of both for generating display images or portions thereof. A user interface comprises one or more display images enabling user interaction with a processor or other device.

An executable application comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

FIG. 1 shows X-ray imaging system 10 for automatically synchronizing display of adjacent different medical image sequences (e.g., DSA image sequences) of a portion of patient anatomy. System 10 includes one or more processing devices (e.g., workstations, computers or portable devices such as notebooks, Personal Digital Assistants, phones) 12 that individually include memory 28, user interface 26 enabling user interaction with a Graphical User Interface (GUI) and display 19 supporting GUI and image presentation in response to predetermined user (e.g., physician) specific preferences. System 10 also includes at least one repository 17, X-ray imaging modality system 25 and server 20 intercommunicating via network 21. Display 19 on processing device 12 presents display images comprising a GUI. At least one repository 17 stores DSA medical image sequences and medical image studies for multiple patients in DICOM compatible (or other) data format. A medical image study individually includes multiple image series of a patient anatomical portion which in turn individually include multiple images. Server 20 includes, contrast agent detector 15, display processor 29 and system and imaging controller 34. X-ray imaging modality system 25 supports automated movement of an X-ray detector 67 and X-ray emitter 65 combination mounted on a C-arm, for example, relative to patient anatomy.

X-ray imaging modality system 25 acquires first and second sets of data at different stages of a treatment procedure representing corresponding first and second image sequences individually comprising multiple temporally sequential individual images of vessels of a portion of patient anatomy. The sequential individual images encompass introduction of a contrast agent into patient vessels. Display 19 presents the first and second image sequences in adjacent areas to facilitate user comparison. Contrast agent detector 15 automatically analyzes the first and second image sequences to identify a first image frame, in both the first image sequence and the second image sequence, indicating presence of a contrast agent. Display processor 29 automatically synchronizes presentation of the first image sequence and the second image sequence in respective areas of the substantially adjacent display areas in response to identification of the first image frame and relative to introduction of contrast agent. Display processor 29 enables a user to synchronously increment through image frames of both the first image sequence and the second image sequence, one image at a time.

Figure 2:
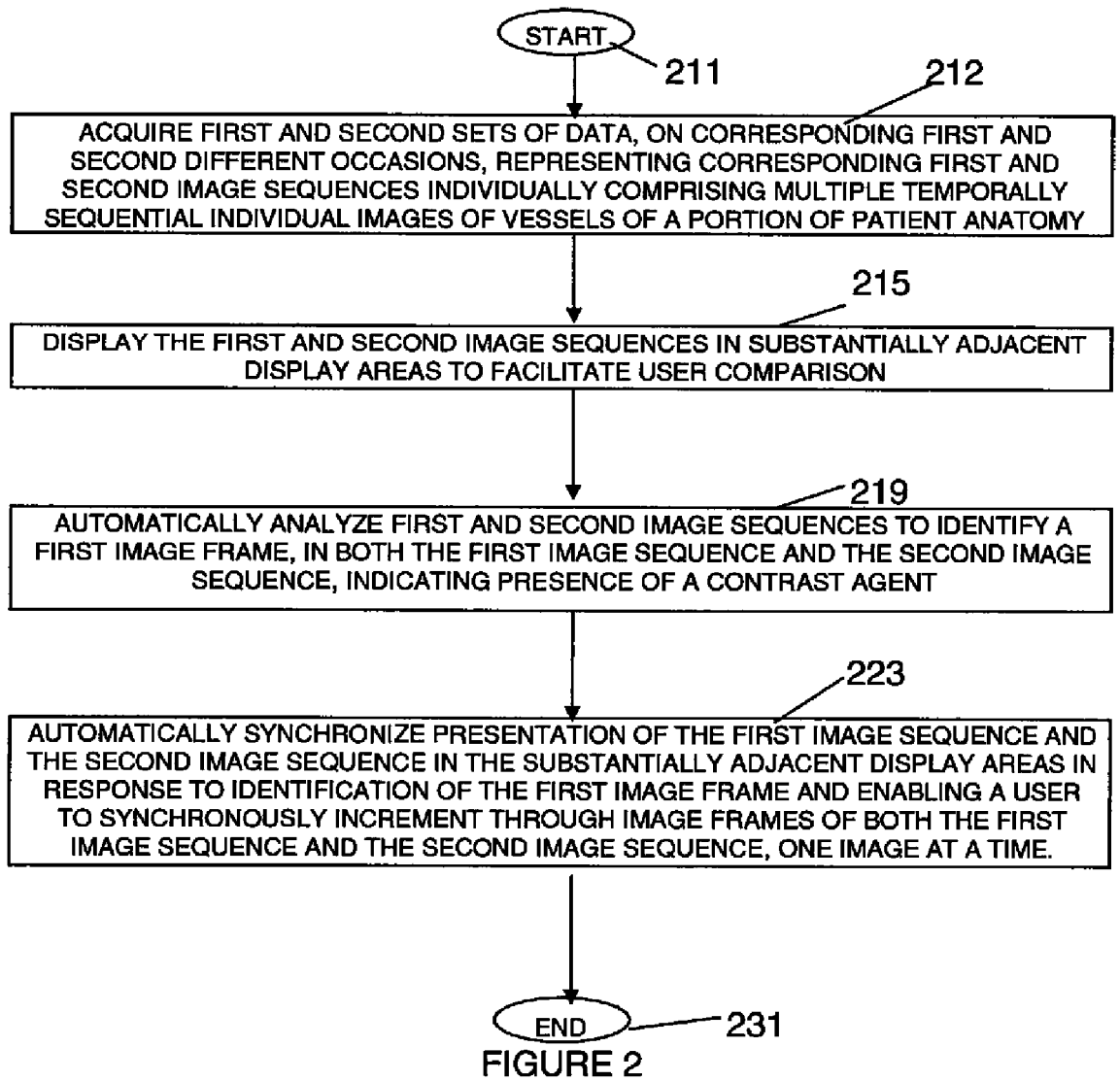
FIG. 2 shows a flowchart of a process performed by a system for automatically synchronizing display of adjacent different medical image sequences of a portion of patient anatomy, according to invention principles.

FIG. 2 shows a flowchart of a process performed by a system for automatically synchronizing display of adjacent different medical image sequences of a portion of patient anatomy. System 10 analyzes individual DSA image sequences to determine a first image frame that contains contrast agent (e.g., a dye). In step 212 following the start at step 211, X-ray imaging modality system 25 acquires first and second sets of data on corresponding first and second different occasions. The first and second sets of data represent corresponding first and second image sequences individually comprising multiple temporally sequential individual images of vessels of a portion of patient anatomy. The first image sequence encompasses a first administration of a contrast agent on the first occasion and the second image sequence encompasses a second administration of a contrast agent on the second occasion after the first image sequence is obtained. The first occasion comprises at least one of, prior to an interventional procedure and a first patient visit and the second occasion comprises at least one of, following an interventional procedure and a second patient visit one or more days after the first visit. In step 215, display 19 displays the first and second image sequences in substantially adjacent display areas to facilitate user comparison and enable a user to synchronously increment and compare before and after procedure medical images.

In step 219, contrast agent detector 15 automatically analyzes the first and second image sequences to identify a first image frame, in both the first image sequence and the second image sequence, indicating presence of a contrast agent. Contrast agent detector 15 processes data representing the first image sequence and the second image sequence to identify the first image frame indicating presence of the contrast agent and a second image frame substantially immediately preceding the first image frame and being substantially exclusive of an indication of presence of the contrast agent, by comparing a difference between measures representative of luminance content of the first and second image frame, with a threshold. Display processor 29, in step 223, automatically synchronizes presentation of the first image sequence and the second image sequence in the substantially adjacent display areas in response to identification of the first image frame and enables a user to synchronously increment through image frames of both the first image sequence and the second image sequence, one image frame at a time. In one embodiment, the time quanta (e.g., frame rate in Hertz) of the first image sequence and the second image sequence are different. In such a case, the first image sequence and the second image sequence do not increment to respective next frames at the same time. Instead, display processor 29 updates the first image sequence and the second image sequence to reflect the frame rate, so that only one image sequence may update. For example, if the first image sequence was acquired at ten frames per second and the second was acquired at five frames per second, a single update step updates the first image sequence but not the second image sequence and the following update step update both image sequences. Display processor 29 concurrently presents the first image frame of both the first image sequence and the second image sequence in adjacent respective areas of the substantially adjacent display areas. Further, display processor 29 in one embodiment generates DSA (digital subtraction angiography) images as the first image sequence and the second image sequence after contrast agent detector 15 automatically analyzes the first and second image sequences to identify the first image frame indicating presence of a contrast agent.

Figure 3:
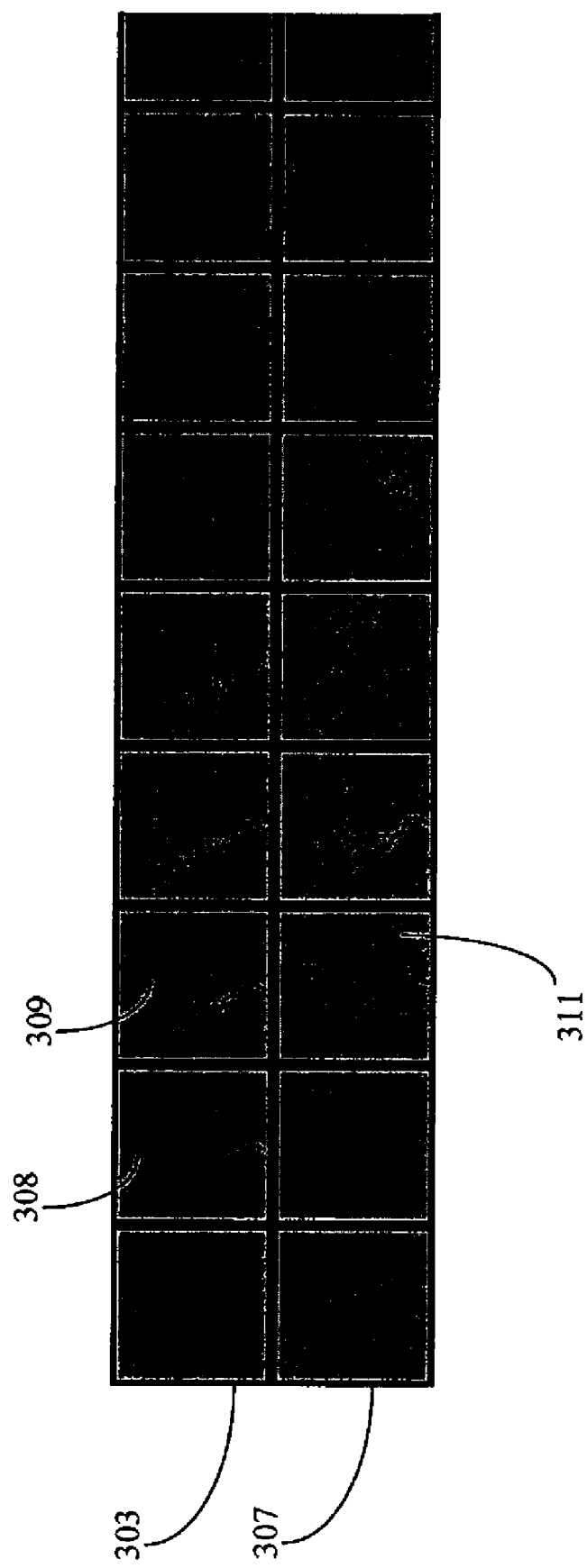
FIG. 3 illustrates un-synchronized adjacent different medical image sequences of a portion of patient anatomy presenting incorrectly correlated frames.

FIG. 3 illustrates un-synchronized adjacent different medical image sequences of a portion of patient anatomy presenting incorrectly correlated image frames. Pre-treatment image sequence 303 is incorrectly synchronized with adjacent post-treatment image sequence 307. Second image frame 308 of image sequence 303 is the first image in sequence 303 indicating presence of a contrast agent. Third image frame 311 of image sequence 307 is the first image in sequence 307 indicating presence of a contrast agent. Image sequences 303 and 307 are incorrectly synchronized so that adjacent image frames 309 and 311, for example, of the different sequences are not correlated.

Figure 4:
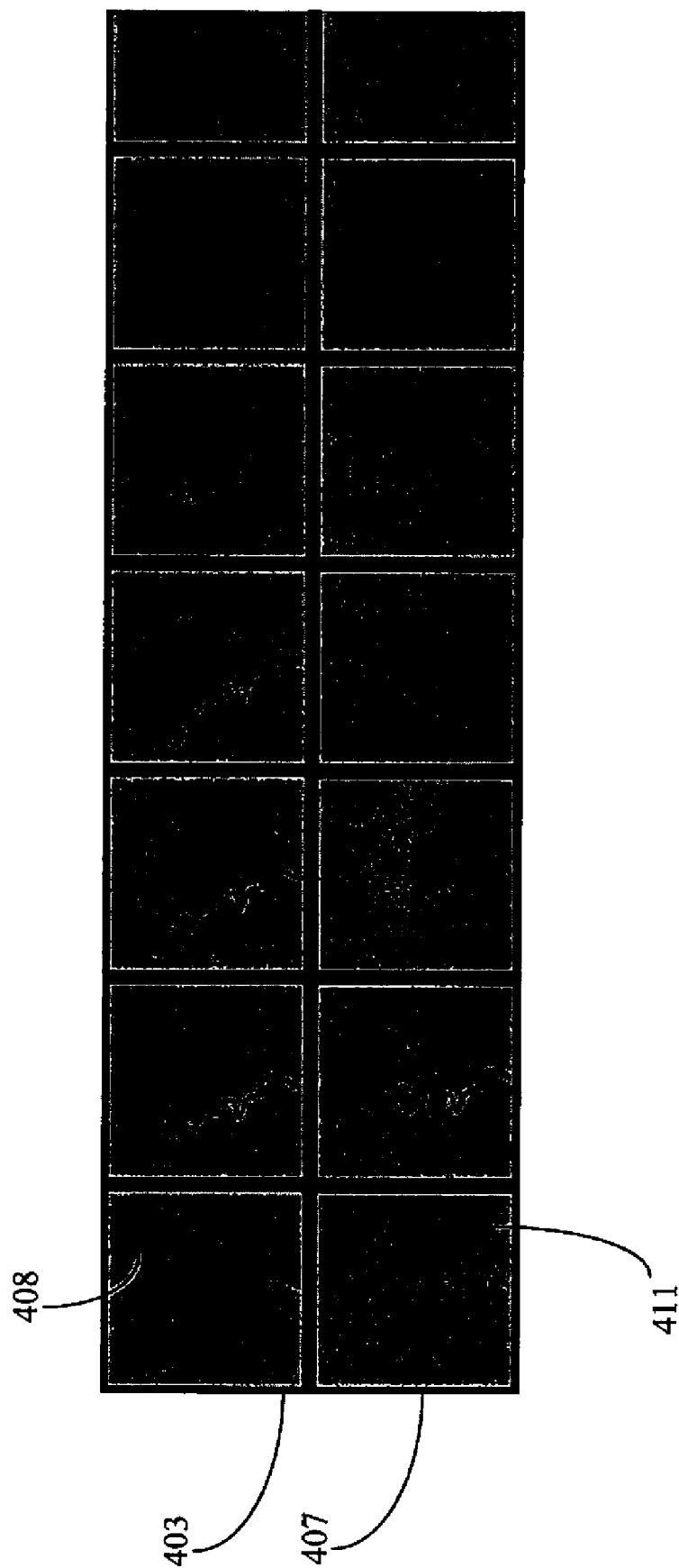
FIG. 4 illustrates synchronized adjacent different medical image sequences of a portion of patient anatomy presenting correctly correlated frames, according to invention principles.

FIG. 4 illustrates synchronized adjacent different medical image sequences of a portion of patient anatomy presenting correctly correlated image frames. System 10 detects a first image frame in image sequences 403 and 407 indicating presence of a contrast agent and synchronizes and aligns the image sequences using the detected frames. Specifically, system 10 detects first image frames 408 and 411 of image sequences 403 and 407 indicating presence of a contrast agent and synchronizes the sequences by aligning frames 408 and 411 so they are adjacent. System 10 presents image frames in sequences 403 and 408 that correspond and excludes other non-correlated image frames. This enables a user to readily see effects of treatment.

In one embodiment, display processor 29 automatically synchronizes presentation of the first image sequence and the second image sequence in respective areas of the substantially adjacent display areas based on a frame preceding or succeeding the first image frame and/or in response to a heart cycle signal. Specifically, display processor 29 in one embodiment automatically synchronizes presentation of the first image sequence and the second image sequence to a point within a heart cycle. User interface 26 enables a user to select a point within a heart cycle at which to synchronize the first image sequence and the second image sequence. Display processor 29 automatically synchronizes presentation of the first image sequence and the second image sequence in respective areas of the substantially adjacent display areas based on an image frame synchronized with a heart cycle signal and closest to time of introduction of contrast agent. System 10 in one embodiment, synchronizes different image sequences in response to both an ECG (Electro-Cardiogram) waveform and detection of contrast agent in an image. The detected contrast agent is used to select a heart cycle in each image sequence and a synchronization point is selected within a selected heart cycle based on the ECG waveform. This advantageously facilitates cardiac function review and diagnosis. Display processor 29 derives measures representative of luminance content of the first and second image frame using at least one of multiple different processes including one process using a histogram derived from pixel grayscale values. The process terminates at step 231.

The system and process of FIGS. 1 and 2 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system automatically determines a synchronization point in two different medical image sequences, e.g., DSA image sequences that typically represent image sequences acquired on different occasions such as different patient visits or pre- and post-treatment. Further, the processes and applications may, in alternative embodiments, be located on one or more (e.g., distributed) processing devices. Any of the functions and steps provided in FIGS. 1 and 2 may be implemented in hardware, software or a combination of both.

What is claimed is:

1. A system for automatically synchronizing display of adjacent different medical image sequences of an anatomical portion derived for use in Angiography or another medical procedure, comprising:

an imaging system for acquiring first and second sets of data at different stages of a treatment procedure representing corresponding first and second image sequences individually comprising a plurality of temporally sequential individual images of vessels of a portion of patient anatomy, said sequential individual images encompassing introduction of a contrast agent into patient vessels;

a display for presenting said first and second image sequences in substantially adjacent display areas to facilitate user comparison;

a contrast agent detector for automatically analyzing said first and second image sequences to identify a first image frame, in both the first image sequence and the second image sequence, indicating presence of a contrast agent; and a display processor for automatically synchronizing presentation of the first image sequence and the second image sequence in said substantially adjacent display areas in response to identification of said first image frame and relative to introduction of contrast agent by adjacently presenting in a single image a plurality of temporally sequential individual images of vessels of a portion of patient anatomy of both said first image sequence and said second image sequence with corresponding individual images of the sequences being adjacent and synchronized and aligned relative to introduction of contrast agent to support comparison and encompassing introduction of a contrast agent into patient vessels.

2. A system according to claim 1, wherein said display processor enables a user to synchronously increment through image frames of both said first image sequence and said second image sequence, one image frame at a time, said first image sequence and said second image sequence comprise DSA (digital subtraction angiography) images and said first image sequence is obtained using a first administration of a contrast agent prior to an interventional procedure and said second image sequence is obtained using a second administration of a contrast agent following an interventional procedure and said substantially adjacent display areas enable a user to synchronously increment and compare before and after procedure medical images.

3. A system according to claim 1, wherein said first image sequence is obtained using a first administration of a contrast agent on a first occasion and said second image sequence is obtained using a second administration of a contrast agent on a second occasion after the first image sequence is obtained and said substantially adjacent display areas enable a user to synchronously increment and compare said first and second image sequences.

4. A system according to claim 1, wherein said display processor generates DSA (digital subtraction angiography) images as the first image sequence and the second image sequence after the contrast agent detector automatically analyzes said first and second image sequences to identify said first image frame indicating presence of a contrast agent and said display processor concurrently presents said first image frame of both said first image sequence and said second image sequence in adjacent respective areas of said substantially adjacent display areas.

5. A system according to claim 1, wherein said display processor automatically synchronizes presentation of said first image sequence and said second image sequence in respective areas of said substantially adjacent display areas based on a frame preceding said first image frame.

6. A system according to claim 1, wherein said display processor automatically synchronizes presentation of said first image sequence and said second image sequence in respective areas of said substantially adjacent display areas based on a frame succeeding said first image frame.

7. A system according to claim 1, wherein said display processor automatically synchronizes presentation of said first image sequence and said second image sequence in respective areas of said substantially adjacent display areas based on an image frame synchronized to a point within a heart cycle signal and closest to time of introduction of contrast agent.

8. A system according to claim 7, including a user interface enabling a user to select a point within a heart cycle at which to synchronize said first image sequence and said second image sequence.

9. A system according to claim 8, wherein said display processor automatically synchronizes presentation of said first image sequence and said second image sequence in respective areas of said substantially adjacent display areas based on an image frame synchronized with a heart cycle signal and closest to time of introduction of contrast agent.

10. A system according to claim 7, wherein said display processor automatically synchronizes presentation of said first image sequence and said second image sequence to a point within a heart cycle.

11. A system according to claim 10, wherein said display processor automatically synchronizes presentation of said first image sequence and said second image sequence in respective areas of said substantially adjacent display areas based on an image frame synchronized to a point within a heart cycle signal and closest to time of introduction of contrast agent.

12. A system according to claim 1, wherein said contrast agent detector processes data representing said first image sequence and said second image sequence to identify said first image frame indicating presence of said contrast agent and a second image frame substantially immediately preceding said first image frame, said second image frame being substantially exclusive of an indication of presence of said contrast agent, by comparing a difference between measures representative of luminance content of the first and second image frame, with a threshold.

13. A system according to claim 12, wherein said display processor derives measures representative of luminance content of said first and second image frame using at least one of a plurality of different processes including one process using a histogram derived from pixel grayscale values.

14. A system for automatically synchronizing display of adjacent different medical image sequences of an anatomical portion derived for use in Angiography or another medical procedure, comprising:

an imaging system for acquiring first and second sets of data, on corresponding first and second different occasions, representing corresponding first and second image sequences individually comprising a plurality of temporally sequential individual images of vessels of a portion of patient anatomy, said first image sequence encompassing a first administration of a contrast agent on the first occasion and said second image sequence encompassing a second administration of a contrast agent on the second occasion after the first image sequence is obtained;

a display for presenting said first and second image sequences in substantially adjacent display areas to facilitate user comparison;

a contrast agent detector for automatically analyzing said first and second image sequences to identify a first image frame, in both the first image sequence and the second image sequence, indicating presence of a contrast agent; and a display processor for automatically synchronizing presentation of said first image sequence and said second image sequence in said substantially adjacent display areas in response to identification of said first image frame by adjacently presenting in a single image a plurality of temporally sequential individual images of vessels of a portion of patient anatomy of both said first image sequence and said second image sequence with corresponding individual images of the sequences being adjacent and synchronized and aligned relative to said first image frame to support comparison and enabling a user to synchronously increment through image frames of both said first image sequence and said second image sequence, one image frame at a time.

15. A system according to claim 14, wherein said imaging system stores in a repository the first image sequence acquired on the first occasion comprising prior to an interventional procedure and said imaging system stores in said repository the second image sequence acquired on the second occasion comprising following an interventional procedure.

16. A system according to claim 14, wherein
said imaging system stores in a repository the first image sequence acquired on the first occasion comprising a first patient visit and said imaging system stores in said repository the second image sequence acquired on the second occasion comprising a different second patient visit one or more days after the first visit.

17. A method for automatically synchronizing display of adjacent different medical image sequences of an anatomical portion derived for use in Angiography or another medical procedure, comprising the activities of:
acquiring first and second sets of data, on corresponding first and second different occasions, representing corresponding first and second image sequences individually comprising a plurality of temporally sequential individual images of vessels of a portion of patient anatomy, said first image sequence encompassing a first administration of a contrast agent on the first occasion and said second image sequence encompassing a second administration of a contrast agent on the second occasion after the first image sequence is obtained;
displaying said first and second image sequences in substantially adjacent display areas to facilitate user comparison;
automatically analyzing said first and second image sequences to identify a first image frame, in both the first image sequence and the second image sequence, indicating presence of a contrast agent; and
automatically synchronizing presentation of said first image sequence and said second image sequence in said substantially adjacent display areas in response to identification of said first image frame by adjacently presenting in a single image a plurality of temporally sequential individual images of vessels of a portion of patient anatomy of both said first image sequence and said second image sequence with corresponding individual images of the sequences being adjacent and synchronized and aligned relative to said first image frame to support comparison.

18. A system for automatically synchronizing display of adjacent different medical image sequences of an anatomical portion derived for use in Angiography or another medical procedure, comprising:
an imaging system for acquiring first and second sets of data, on corresponding first and second different occasions, representing corresponding first and second image sequences individually comprising a plurality of temporally sequential individual images of vessels of a portion of patient anatomy, said first image sequence encompassing a first administration of a contrast agent on the first occasion and said second image sequence encompassing a second administration of a contrast agent on the second occasion after the first image sequence is obtained;
a display for presenting said first and second image sequences in substantially adjacent display areas to facilitate user comparison;
a contrast agent detector for automatically analyzing said first and second image sequences to identify a first image frame, in both the first image sequence and the second image sequence, indicating presence of a contrast agent; and
a display processor for automatically synchronizing said first image sequence and said second image sequence to a point within a heart cycle and in response to identification of said first image frame by adjacently presenting in a single image a plurality of temporally sequential individual images of vessels of a portion of patient anatomy of both said first image sequence and said second image sequence with corresponding individual images of the sequences being adjacent and synchronized and aligned relative to said first image frame to support comparison and enabling a user to synchronously increment through image frames of both said first image sequence and said second image sequence in the substantially adjacent display areas, one frame at a time.

19. A system according to claim 18, wherein
said display processor automatically synchronizes presentation of said first image sequence and said second image sequence in respective areas of said substantially adjacent display areas based on an image frame synchronized to a point within a heart cycle signal and closest to time of introduction of contrast agent.

* * * * *